United States Patent [19]

Fan et al.

[11] Patent Number: 5,417,979
[45] Date of Patent: May 23, 1995

[54] COMPOSITION OF HERBAL EXTRACTS

[75] Inventors: Sophie Fan, Millwood, N.Y.; Xuhui Wang, Shanghai, China

[73] Assignee: International Medical Research, Inc., Placentia, Calif.

[21] Appl. No.: 145,770

[22] Filed: Nov. 2, 1993

[51] Int. Cl.⁶ .......................... A61K 9/14; A61K 9/20; A61K 9/48; A61K 35/78
[52] U.S. Cl. .................. 424/451; 424/195.1; 424/464; 424/489
[58] Field of Search ...................... 424/195.1, 451, 465, 424/489, 464, 423, 422

[56] References Cited

U.S. PATENT DOCUMENTS

3,843,788 10/1974 Iwasa et al. ...................... 424/195.1
5,198,230  3/1993 Wen ................................. 424/525

Primary Examiner—Thurman K. Page
Assistant Examiner—James M. Spear
Attorney, Agent, or Firm—Charles J. Herron

[57] ABSTRACT

A composition comprising a selected combination of herbs and their extracts. Properties of the composition include dietary supplement, appetite stimulant, analgesic and mood elevation utilities, particularly advantageous for broad spectrum improvement in quality of life for terminally ill individuals. This supplement is found to profoundly improve patients' appetites and immune system. It can also largely reduce patient's pain and thus improve patients' mood.

17 Claims, 7 Drawing Sheets

COMPOSITION OF HERBAL EXTRACTS

BACKGROUND OF THE INVENTION

The vast majority of terminally-ill individuals require dietary supplement, appetite stimulation, significant analgesia and/or mood elevation to optimize the quality of the duration of their survival prognosis.

The principal major analgesics belong to the morphine opioids. This class of drugs acts by blocking the central nervous system. Non-opioid drugs that are used are nonsteroid anti-inflammation drugs (NSAIDS), such as aspirin. This latter class of drugs inhibits prostaglandin synthesis and thus reduces the pain transmitted by somatic nerves. None of these are entirely ideal due to the addictive effect of the first class of drugs and the often limited efficacy of the second class of drugs. Neither have ever been shown to exhibit appetite stimulant properties in the absence of dependence risk.

SUMMARY OF THE INVENTION

In accordance with the present invention, the inventors have provided a composition comprising a preparation of each of the following components: Cheng-min chou, Mou-hui Tou, Stephania Sinica Diels, Stephania Delavayi Diels, Zanthoxylum Nitidum, Corydalis Bulbosa, Lycoris Radiata, and Agrimonia Pilosa Ledeb. Most preferred is the above composition further comprising a preparation of each of the following components: Pyrola Rotundifolia L., Rabdosia Rubescerts, Ganoderma Japonicum. Flower Pollen, Panax Ginseng, Cervus Nippen Temminck, and Glycyrrhiza.

The above combination of herbs and their extracts is useful as a food or nutritional supplement and has been observed to profoundly improve individuals appetites and stimulate their immune system responsiveness. It also significantly reduces pain in individuals receiving it and thus improves these patients' mood.

DETAILED DESCRIPTION

A principal aspect of the present invention is a composition of a preparation (e.g. dried, cut herbs or extracts thereof) from each of the following components: Cheng-min chou, Mou-hui Tou, Stephania Sinica Diels, Stephania Delavayi Diels, Zanthoxylum Nitidum, Corydalis Bulbosa, Lycoris Radiata, and Agrimonia Pilosa Ledeb. Most preferred is the above composition further comprising a preparation of each of the following components: Pyrola Rotundifolia L., Rabdosia Rubescens, Ganoderma Japonicum, Flower Pollen, Panax Ginseng, Cervus Nippon Temminck, and Glycyrrhiza.

Certain of the individual extracts in this composition are new compositions of matter in and of themselves. They are extracts and other therapeutically effective preparations of Cheng-min chou and, independently, of Mou-hui Tou.

EXAMPLE 1

Preparation of Extract Compositions

Preparation Components

As used herein, Preparation A contains material from each of the following: Cheng-min chou, Mou-hui Tou, Stephania Sinica Diels, Stephania Delavayi Diels, Zanthoxylum Nitidum, Corydalis Bulbosa, Lycoris Radiata, and Agrimonia Pilosa Ledeb and a preparation of each of the following components: Pyrola Rotundifolia L., Rabdosia Rubescens, Ganoderma Japonicum, Flower Pollen, Panax Ginseng, Cervus Nippon Temminck, and Glycyrrhiza. Preparation B contains material from each of the following: Cheng-min chou, Mou-hui Tou, Stephania Sinica Diels, Stephania Delavayi Diels, Zanthoxylum Nitidum, Corydalis Bulbosa, Lycoris Radiata, and Agrimonia Pilosa Ledeb.

Extract Preparation: The procedure used for preparing extracts of each of the components was as follows: A cut, dried portion (100 g) of each of the above ingredients was individually finely chopped by blender, the chopped preparation was soaked in water (300–500 ml) for a minimum of 1 hour, boiled for 20–50 minutes; and allowed to cool to ambient temperature.

The solid residue of the above was filtered through a 1.0 L Buchner funnel lined with Whatman filter paper. Volumes of ethanol equal to each sample filtrate volume were added to the flask and the mixture was vigorously stirred until precipitation was complete. The filter residue was discarded and the aqueous phase eluate lyophilized. The resultant material was used as is.

The components prepared as described above were combined by addition to a powder mixer (Won-Nen Mixer, Model 8L-K-III, Shanghai). The weight of Lycoris Radiata used was defined as 1, the relative weights of the rest of the ingredients were 0.5 to 2, except Cervus Nippon Temminck which was between 0.01 to 0.2.

EXAMPLE 2

Analgesic Effect of the Composition(s)

Four series of Wistar White rats (8 rats per series; 300 g avg. body weight) were treated as follows.

Series 1: Abdominal injection of 1 ml saline solution (0.9% NaCl)—control group

Series 2: Abdominal injection of 1 ml Preparation B (4.5 mg)

Series 3: Abdominal injection of 1 ml Preparation A (9 mg)

Series 4: Abdominal injection of 1 ml morphine (0.75 mg)

Each rat received an abdominal injection consistent with the series to which it had been assigned and was then placed into a mechanical restraint. The restraint devices were provided with electrodes that produced a mild electric shock sufficient to cause twitching of the tails of the rats. The degree of response in each of the rats in each series was recorded as the length of time required to interrupt the circuit at time intervals after injection of 0 (substantially immediately upon restraint), 15, 30, 45, 60, 75, 90 and 105 minutes.

Figures 1, 2:
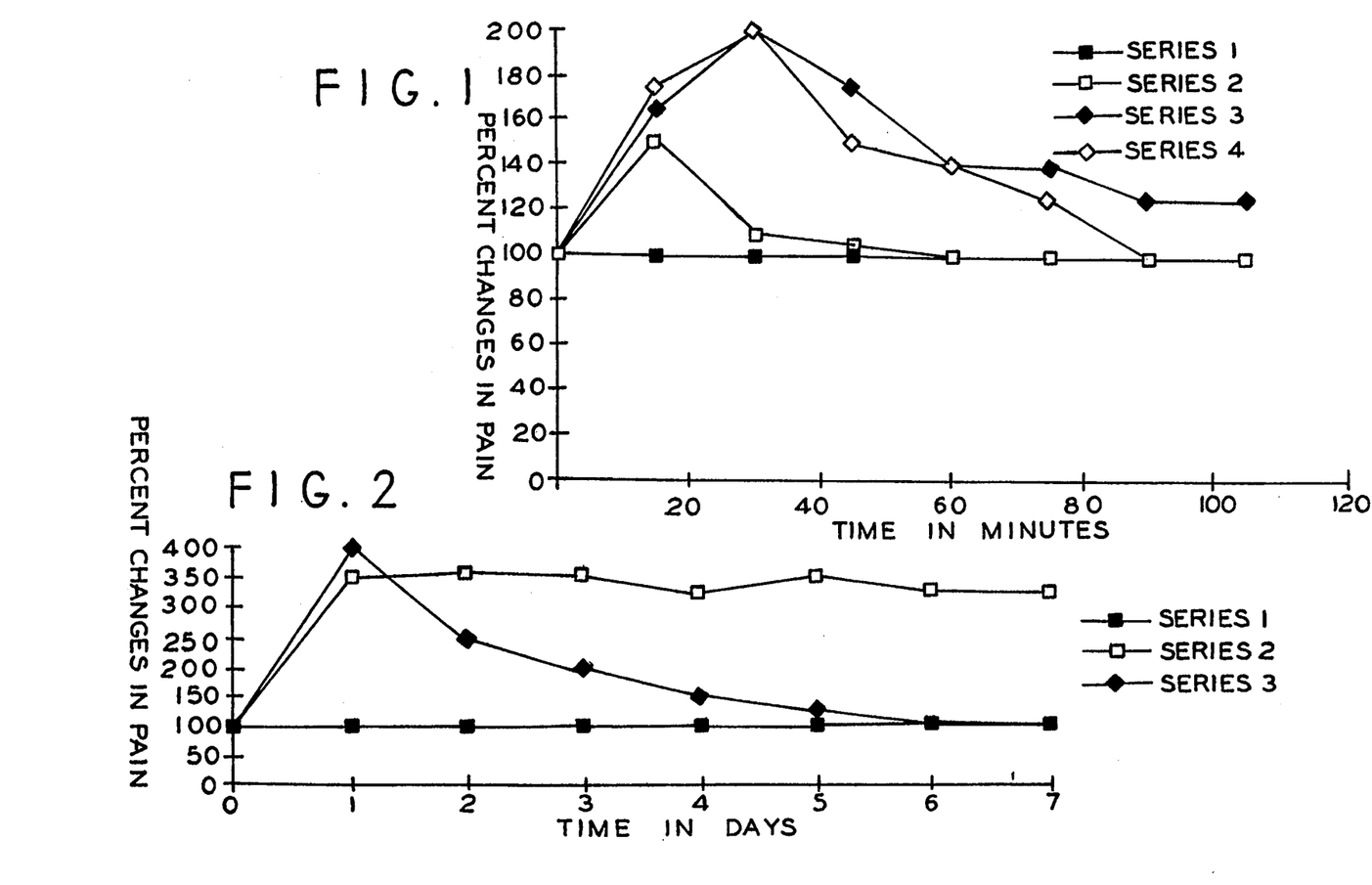
FIG. 1 graphically illustrates the comparative voltage outputs at each time interval as the mean observed for each series of animals tested in Example 2. The degree of twitching response in control series 1 was defined as 100%. Preparation A (used at 12× the morphine concentration) resulted in a more pronounced inhibition than even the morphine-treated series displayed. Preparation B (series 2) animals demonstrated less pronounced inhibition than either Preparation A or the morphine group animals.
FIG. 2 graphically illustrates the comparative levels of analgesic effect of Preparation A and morphine as tested in Example 3 over time. While the effect of morphine declined continuously from day 2 until day 7, the effect of the preparation of the invention remained undiminished throughout the observation period of 7 days.

FIG. 1 graphically summarizes the comparative responses at each time interval as the mean observed for each series. The twitching response delay time in control series 1 was defined as 100%. Preparation A of series 3 (used at 12× the morphine concentration) resulted in a more pronounced inhibition (long delay time) than even the morphine-treated series (series 4) displayed.

EXAMPLE 3

Duration of Analgesic Effect

Three groups of Wistar White rats (8 rats per group) were used in this study and treated as follows. The experimental procedures used were the same as those described in the Example 2, except as follows:

Series 1: Abdominal injection of 2 ml of saline solution (0.9% NaCl)—control group Series 2: Abdominal injection of 2 ml of Preparation A (20 mg)

Series 3: Abdominal injection of 2 ml of morphine (3 mg)

The animals were each injected once daily for seven consecutive days. Response in each animal was recorded 10 minutes after injection on each day. FIG. 2 graphically illustrates the comparative levels of analgesic effect of Preparation A and morphine over time. While the effect of morphine declined continuously from day 2 until day 7, the effect of Preparation A remained undiminished throughout the observation period of 7 days.

EXAMPLE 4

Comparative Addictive Effect

Experiment 1

Three groups of Chinese Kun-Min mice (10 mice per group; 19±1 g each) were used in this study. The first group was injected with 1 ml of saline solution (0.9% NaCl), the second group with 1 ml of morphine (0.5 rag), the third group with 1 ml of Preparation A (6 mg). The animals were injected abdominally, twice daily (8 hours apart) for four consecutive days. The dosage for the last injection was doubled. Behavior of the mice was observed on day four. Group 1 and Group 3 showed normal generally tranquil behavior, while the mice in Group 2 displayed an abnormal excited state.

Experiment 2

Two groups of Wistar White rats (10 rats per group) were treated as follows. The first group was injected with 1 ml of morphine (0.75 mg) and the second group was injected with 1 ml of Preparation A (10 mg). After the abdominal injections, the stiffness of the tails were monitored for 10 minutes. The first group showed a very stiff tail which could be manipulated to any shape, while the second group showed a normal relaxed tail.

EXAMPLE 5

Study on Human Volunteers

Twenty-two individuals who had been diagnosed to be in the terminal stages of cancer and were being treated with chemotherapy agents such as Piminodinum, Dolantinum and Dihydroetorphine volunteered for this study. The types of cancers diagnosed in the volunteer population were as follows:

| | |
|---|---|
| Hepatoma patients | 6 |
| Metastatic Leukemia patients | 4 |
| Lung cancer patients | 4 |
| Colon cancer patients | 3 |
| Esophogus cancer patients | 1 |
| Stomach cancer patients | 2 |
| Breast cancer patients | 1 |
| Pancreas cancer patients | 1 |

By consent, chemotherapy treatment was discontinued and thereafter each patient was given 600–1800 mg of Preparation A daily for 7 consecutive days. At the end of one day of treatment with Preparation A, the patients responded to the questions summarized in Table 1.

TABLE 1

| Questions | Degree of pain (scale 0-10) | |
|---|---|---|
| | Day 0 | Day 1 |
| Worst pain in the past 24 hours | 6–9 | 0–3 |
| Average pain at the present time | 3–5 | 0–3 |
| How much interference in your daily activities due to discomfort | 6–9 | 0–3 |

The responses appearing in Table 1 are the range of response to each question from the 22 patients. This clearly demonstrates that patients who received Preparation A experienced a profound reduction in the pain associated with their condition.

At day 7, the erythrocyte sedimentation rate (ESR) of each patient was measured and compared with that patient's ESR at Day 0. At day 21, the total white cell count of each patient was measured and compared to that patient's WBC count at Day 0. The range of results are set forth in Table 2.

TABLE 2

| Parameters | Day 0 | Day 7/Day 21 |
|---|---|---|
| ESR | 35–120 | <30 (Day 7) |
| WBC counts | 3000–3500/nm$^3$ | 5500–7500/nm$^3$ |

EXAMPLE 6

Supplemented Extract Compositions

The components used in this preparation includes the components used in Example 1 and one additional component, goat's milk. The preparation protocol is basically the same as that described in Example 1, except dried goat milk powder (weight 0.5 to 2) was also included in the herbal composition before mixing. The final product was sifted through a 0.2 micron filter to ensure the homogeneity in powder.

EXAMPLE 7

Hepatoma Cell Lysis By Herbal Extract Light And Microscopic Studies

Optical (light microscopy) and scanning and transmission electronmicro graphs were used in this study to observe the morphological and ultrastructural changes of hepatoma cells exposed to a composition as described in Example 6.

SMMC7721 hepatoma cells with a titer of 250,000 per ml (from Cancer Research Institute, Shanghai, China) were cultured for 24 hours in 5% $CO_2$ at 37° C. following a standard protocol (Sigma cell culture reagent, DMEM), in a total of 36 culture dishes. Each dish was covered with a coverglass (carbon-sprayed surface). At the end of 24 hours, the dishes were divided into 2 groups (16 dishes per group) as follows:

Group 1: control group, i.e., no herbal extract composition.

Group 2: treated group: 200 μg of extract composition per dish.

Cell samples from each group were examined under the microscope at time intervals of 4 hours, 12 hours and 24 hours. Three cell samples were used for each examination. Each cell sample was examined under a light microscope (Olympus) before being examined by electron microscopic observation.

Surface structures of the hepatoma cells were examined using a JEOL JXA-840 scanning electron microscope. Cultured cells were dipped in a precooled glutaraldehyde solution 2.5%, dried and coated with gold particles by an ion sprayer (FME COAT JEF-1100).

Ultrastructures of the hepatoma cells were examined by transmission electron microscopy using a JEOL JEM-1200. Cultured cells were recovered and dipped in a precooled glutaraldehyde solution (2.5% ). After 2 hours, the cells were washed three times with phosphate buffer (pH 7.4) and fixed with 1% osmic acid. After fixing, the cells were again washed with phosphate buffer, dried with 75% ethanol, implanted into agar, and embedded with Epon 812 which was polymerized at 60° C. Ultrathin sections (~500 A vigstroms) were prepared and stained with uranium acetate and lead citrate.

Figure 3A:
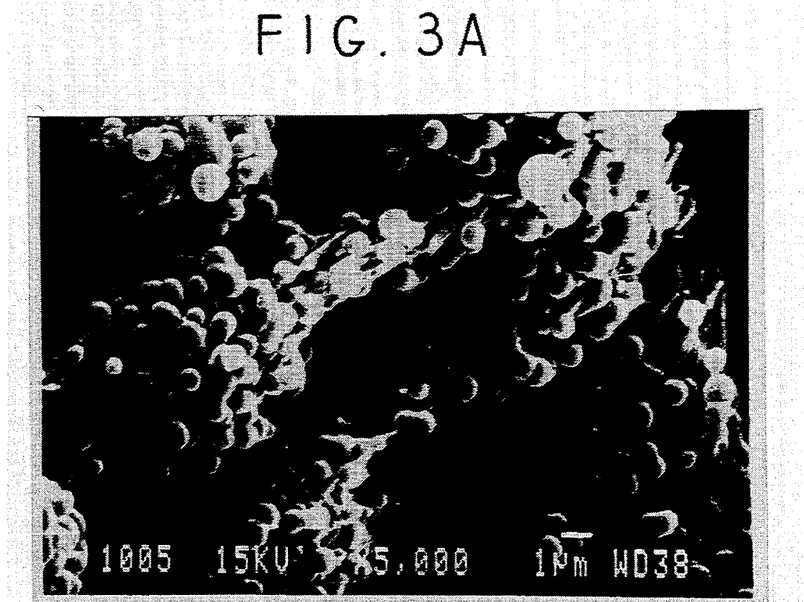
FIGS. 3–10 are microscopic views showing hepatoma cell structures with and without the effects from contacting the herbal extract compositions.
Figure 3B:
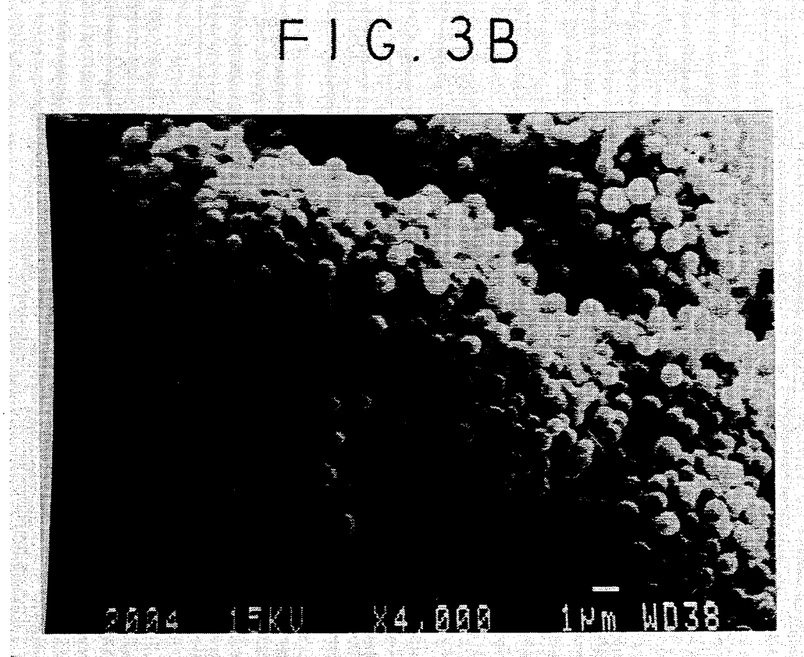
Figure 4A:
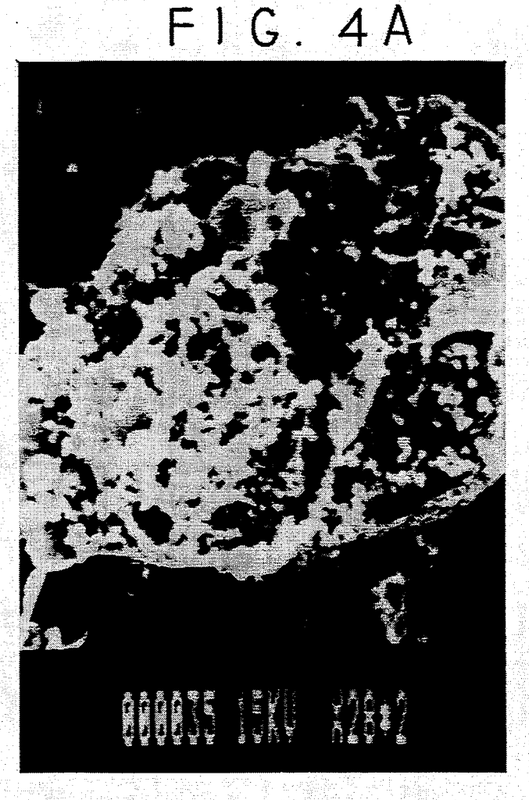
Figure 4B:
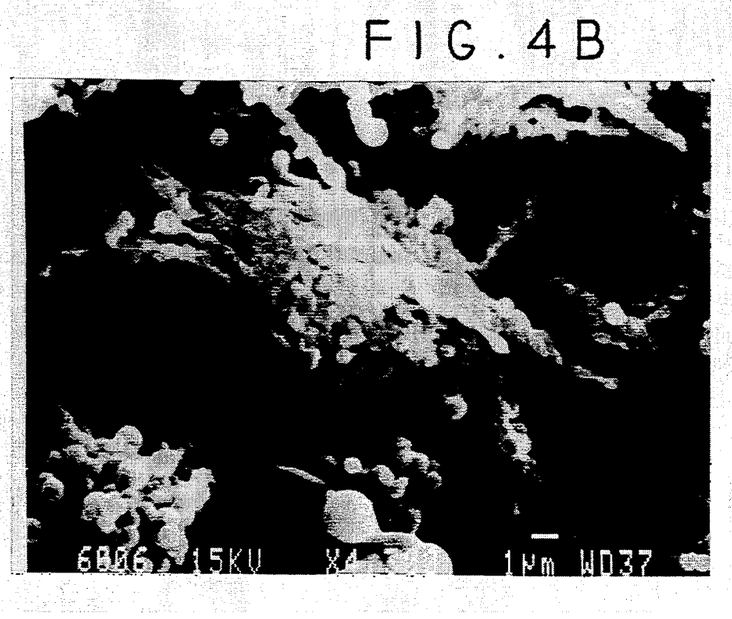
Figure 5:
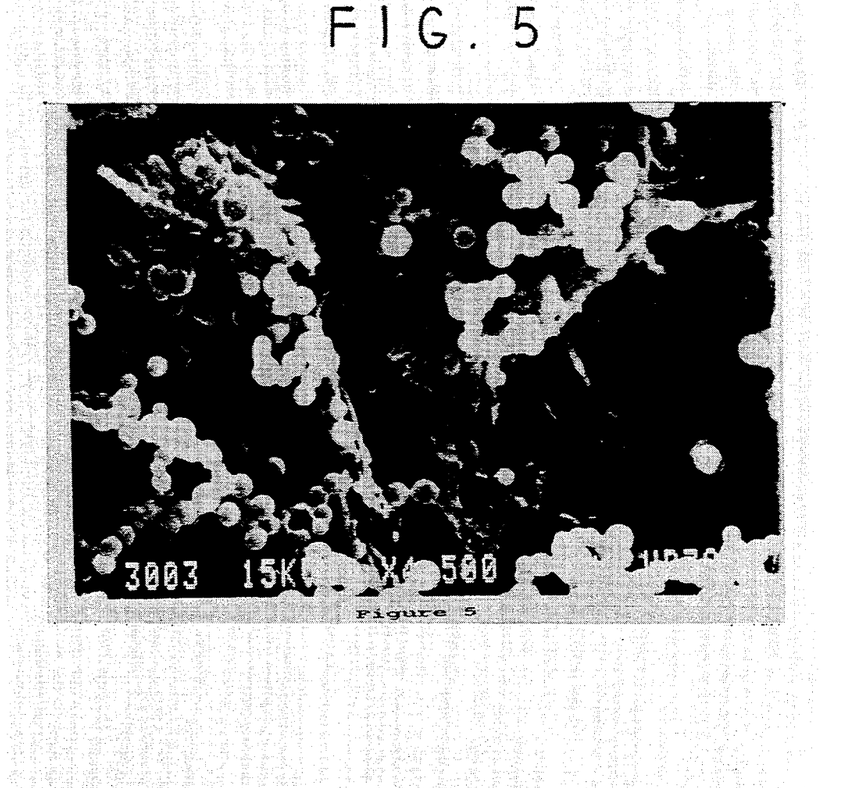

FIGS. 3A and 3B show the growth of hepatoma cells from Group 1 (control) at time 12 hours and 24 hours. It is evident that these cells proliferated very rapidly and had formed cell clumps by 12 hours. It is also evident that the cell surfaces were covered with many secretory granules and that the cells were linked by hairy projections at 24 hours. In stark contrast, in the Group 2 treated cells the composition that many surface granules showed disruption on cell membranes after 12 hours (FIG. 4A). After 24 hours, the number of cell population decreased profoundly (FIG. 4B). In addition, the connection between cells were largely destroyed and the cell membranes disintegrated (FIG. 5).

Figure 6:
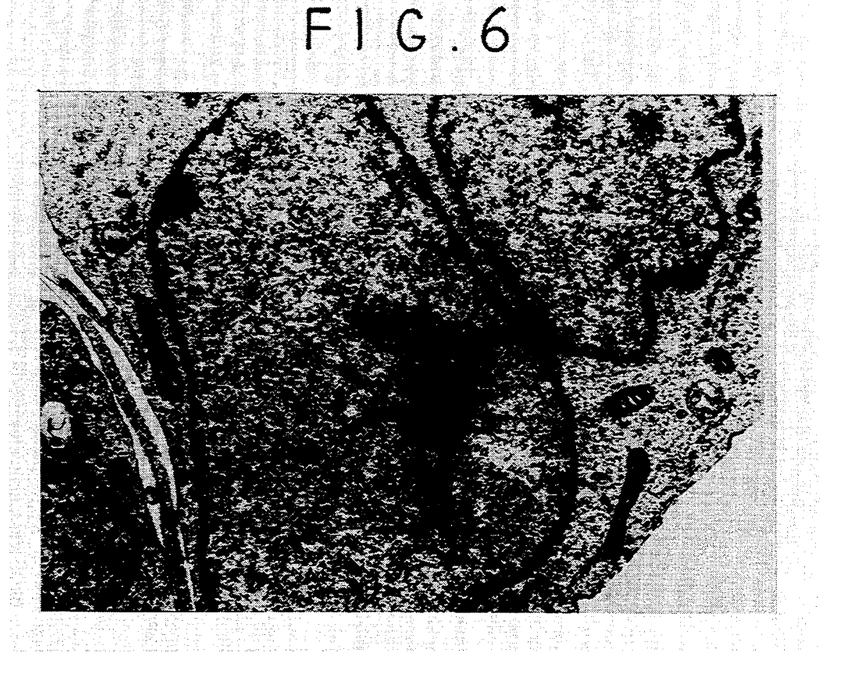
Figure 7:
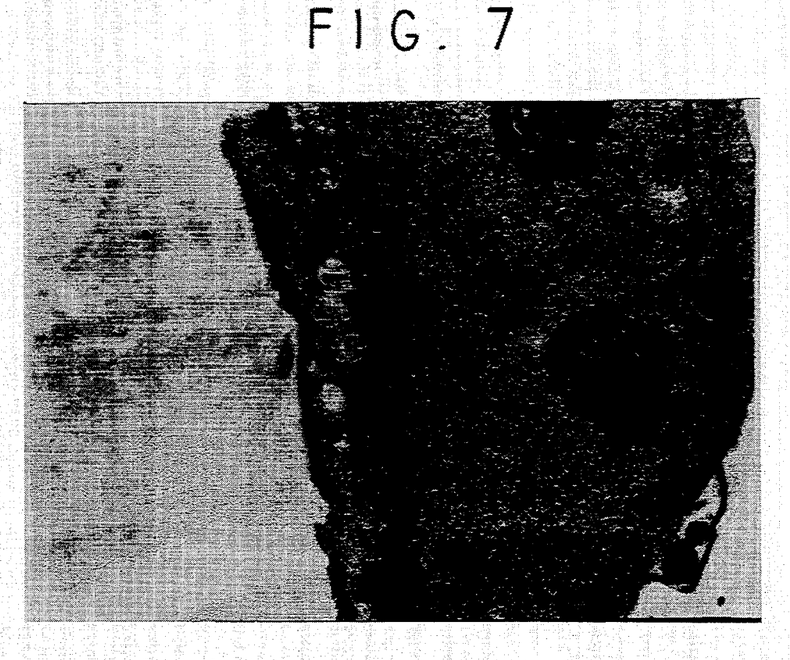
Figure 8:
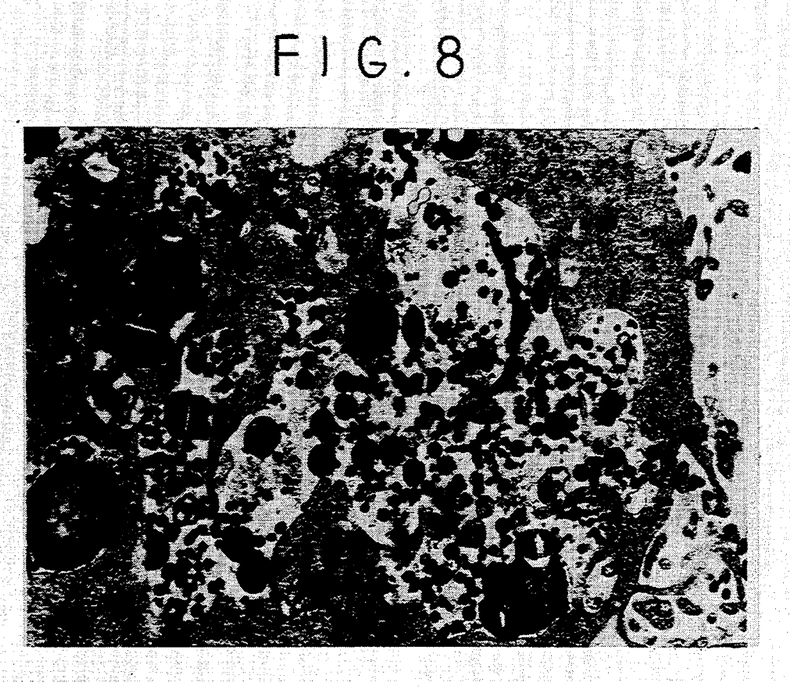
Figure 9:
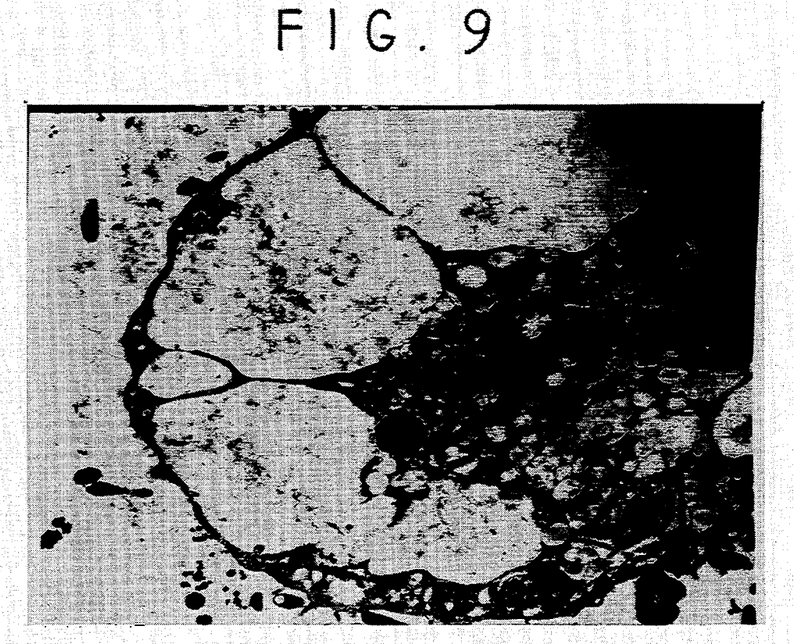
Figure 10:
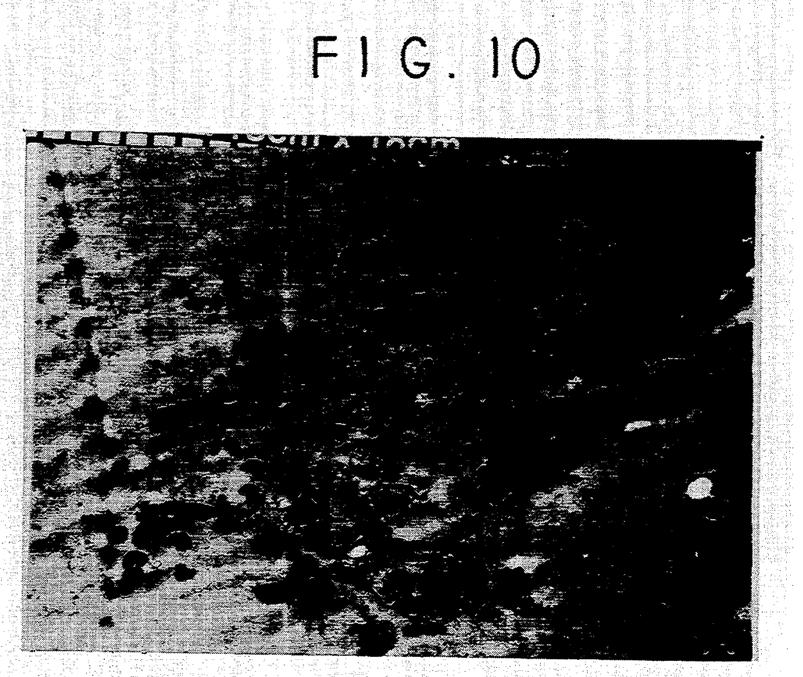

To confirm the above observations, data from a transmission EM study were compared. FIG. 6, 7, and 8 display the inner structures of the cells with and without the effect of the extract composition respectively at 12 hours. While there were multinucleic and disordered organelles seen in the malignant cell (12 hr./untreated) (FIG. 6), a more ordered inner structure of the treated cells was observed in FIG. 7 (12 hours). Furthermore, the herb-treated cells exhibited a clear endocytosis of the herbal particles through the surface cell membranes. At the same time, herbal particles entered into the nucleus through the nuclear envelope: some entered into nucleolus (FIG. 7) and some stayed in the nucleus (FIG. 8). At 24 hours after the herbal treatment, the hepatoma cells were disintegrated as shown in FIG. 9 and 10. The above results clearly indicate that the herbs can effectively enter into nucleus and kill the hepatoma cells.

EXAMPLE 8

Suppression of N-ras Gene Transcription

Since the EM data showed a specific interaction between the herbal particles of the extract composition and the nucleus, the decision was made to investigate the effect of the herbs at the gene level. Hepatoma cells are known to over express N-ras mRNA (Rolf Muller et al. Nature, 229:640, 1982). In this study we determined and compared the contents of mRNA of hepatoma cells transcribed from mouse DNA, with and without treatment using the extract.

Ten male nude mice were inoculated with human primary hepatoma tissue segments of 3 mm$^3$ in size. The hepatoma tissues were obtained from three hepatoma patient volunteer donors in Shanghai. After tumor transplant, the mice were raised using routine maintenance for 3 days. At the end of three days, the mice were randomly divided into two groups (5 mice per group):

Group 1: The control group, 0.2 ml of saline solution (0.9% Na Cl) was injected to the tumor site in each mouse every other day for 6 days.

Group 2: The treated group, 0.2 ml of the herbal extract (400 μg) was injected to the tumor site in each mouse every other day for 6 days.

The mice were sacrificed on day 7 of the study. The tumors were removed and processed for N-ras mRNA determination.

The weighted tumors (~3 gram) were cut into pieces and homogenized in a buffer containing 0.5% SDS, 2.5 mM EDTA, 0.14 M NaCl, 25 mM TrisHCl and 1.2 mg/ml hepamin at pH 7.6 and at 4° C. RNA was isolated according to the procedure of Land et al. (Nucleic Acid Res. 9:2251, 1981). The poly(A)-terminated mRNA was prepared by the method of Aviv and Leder (Proc. Nat. Acad. Sci. U.S.A., 69: 1408, 1972). The analysis of mRNA was by electrophoresis in formaldehyde gels, followed by Northern hybridization and autoradiograph (Maniatis et al., Molecular Cloning—A Laboratory Manual, second edition, Cold Spring Harbor Laboratory Press, 1989). The probe used for hybridization was $^{32}$P-dTTP radiolabeled (400 uCi/mmol) and obtained from Amersham.

Figure 11:
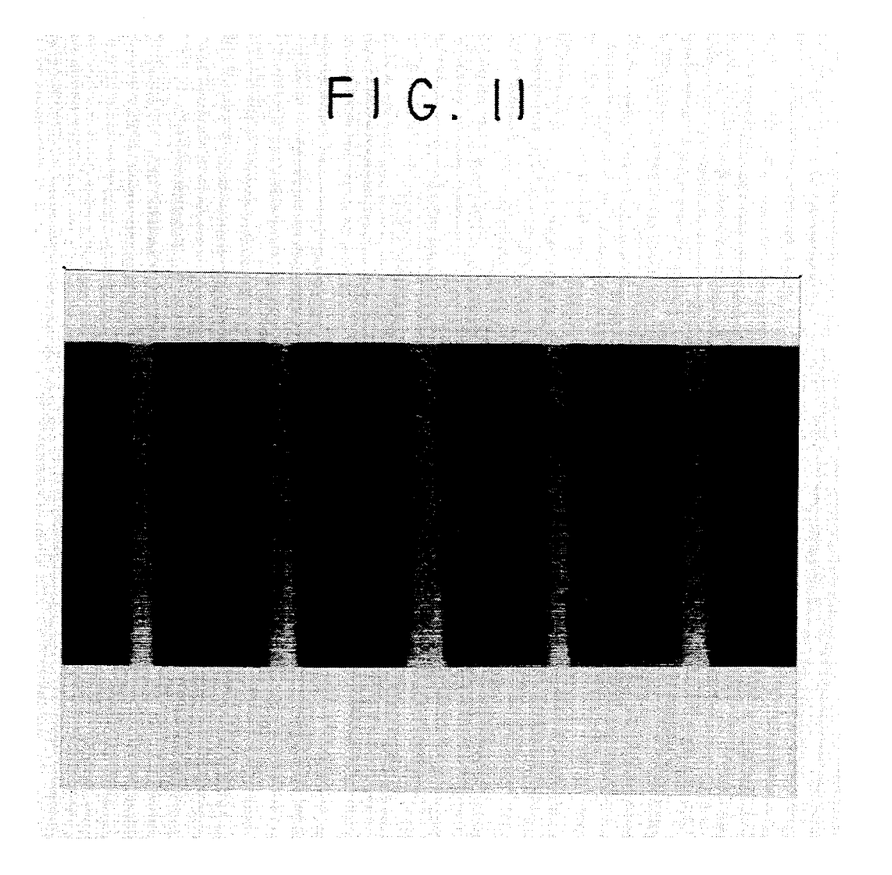
FIG. 11 is a photograph of the auto radiographs of MRNA isolated in the study of the herbal extract compositions and cell structures.

FIG. 11 is a photograph of the autoradiographs of mRNA isolated above. The mRNA analysis experiments were carried in triplicate. Lanes 1-3 and lanes 4-6 exhibit the quantities of mRNA of the N-ras gene obtained from the treated and untreated mice, respectively. While absolutely no band straining was present for material obtained from the treated subjects, large bands clearly identifiable as N-ras RNA were observed for the untreated mice. Nondetectable bands were seen for the treated mice. These results indicate that the extract composition effectively suppressed the transcription of the N-ras gene. This finding contribute to our understanding of the likely mechanism of action of the extract composition for its anti-hepatoma effect.

EXAMPLE 9

Inhibition of Cancer Growth In Vivo

An in vivo mouse model was used to study the effect of the extract composition on hepatoma growth rate.

Sixty male nude mice were inoculated with Bel 7402 hepatoma cells and were grown under a routine protocol. About 1-2 weeks later, 40 mice with tumors of about 1.8±0.6 cm$^3$ were selected for the experiment. The size of the tumor was measured as follows (longest side being the reference length).

The forty mice were divided into three groups:

Group 1 (10 mice): Control group, 500 ul of the saline solution was injected to the tumor site every other day for six days.

Group 2 (20 mice): Treated group, 500 ul of herbal extract (500 μg) was injected to the tumor sites every other day for six days.

Group 3 (10 mice): Blank group, the mice in this group was not injected with any solution.

On day 7, the tumor size of each mouse was measured as above. The mice were then sacrificed and the tumors removed, dried by filter paper and weighed with an accuracy to within one (1) μg.

Table 3 summarizes the average size and average weight of the tumor in each mouse group. The size and the weight of the tumors in Group 2 were profoundly reduced compared t that of the Group 1 and Group 3. Furthermore, the difference in Group 1 and Group 3 was not significant. These data provide scientifically recognized relevant evidence that the extract composition effectively inhibits human solid tumor hepatomas.

TABLE 3

| Group | Sample # | Tumor Size (cm$^3$) | Tumor Weight (g) |
|---|---|---|---|
| 1 | 10 | 3.7 ± 0.81 | 3.9 + 0.8 |
| 2 | 20 | 1.3 ± 0.74 | 1.4 + 0.5 |
| 3 | 10 | 4.0 ± 0.78 | 4.3 + 0.7 |

As is evident from the results reported in Table 2, a clear improvement in the white blood cell counts and in red cell sedimentation rate was observed.

EXAMPLE 10

Effect of the Extraction Composition on Brain of Acetylcholine Level

The effect of the herbal extract on acetylcholine concentration in mouse was studied below.

1) Animal model

Twenty-four male Wistar mice (200±5 g each) were randomly divided into 3 groups (8 mice per group):

Group 1: Control group, abdominal injection of 1 ml saline to each normal mouse

Group 2: Contrast group, each of the normal mouse was subject to electric shock to induce pain (same protocol as that described in the previous patent application Ser. No. 08/048,859 and immediate after was injected with 1 ml saline to abdominal cavity.

Group 3: Treated group, each of the normal mouse was subject to electric shock to induce pain and immediate after was injected with e ml herbal extract (12 mg) to abdominal cavity.

2) Detection of acetylcholine concentration in brains:

Thirty minutes after injection of herb extract or saline, mice were sacrificed. The brain from each mouse was removed and the cerebella portion was discarded. After weighing, the brains were immediately soaked in 10 volume of precooled 0.11M HClO$_4$ solution and homogenized. The homogenate was incubated in icebath for 30 minutes and centrifuged at 15000 rpm for 15 minutes at 4° C. The supernatant was collected for acetylcholine determination.

The radio immunoassay was performed for the detection of acetylcholine concentration. The antibody used for assay was obtained from shanghai Academy of Science Laboratories with a titer of 1:1000. The radiolabelled acetylcholine. [$^3$H] Ach was purchased from Amersham. The radioactivity was 925×10$^{10}$ mCi. The measurements were carried out in triplicate.

Results obtained from above are presented in Table 4. It is clear that the brain level of acetylcholine in the herb-treated mice increases significantly, an increase of 70%. In contrast, the change in acetylcholine concentration in the contrast group is not as profound. These date demonstrate that the herbal extract can effectively boost the brain level of acetylcholine in-vivo. since it is well established that Alzheimer disease can be improved by agents which increase brain level of acetylcholine (Proc. Natl. Acad. Sci. USA, 90, 9031, 1993), our experimental results suggest that the herbal extract can also be used to treat Alzheimer disease.

TABLE 4

| Group | Sample # | Acetylcholine Concentration (n mol/g brain) |
|---|---|---|
| Control | 8 | 22.2 + 2.5 |
| Contrast | 8 | 26.4 + 18.9 |
| Herb-treated | 8 | 37.6 + 6.1 |

What is claimed is:

1. A composition comprising a mixture of dried ethanol extraction eluates of residues obtained from boiling water extraction of cut, dried portions of Lyeotis Radiata, and Cheng-min chou, Mou-hui Tou, Stephania Sinica Diels, Stephanie Delavayi Diels, Zanthoxylum Nitidum, Corydalis Bulbosa and Agrimonia Pilosa Ledeb in weight ratio ranges with Lycoris Radiata of 1:0.5-2, 1:0,5-2, 1:0,5-2, 1:0.5-2, 1:0.5-2, 1:0.5-2 and 1:0.5-2, respectively.

2. The composition of claim 1 which further comprises dried ethanol extraction eluates of residues obtained by boiling water extraction of cut, dried portions of Pyrola Rotundifolia L., Rabdosia Rubescens, Ganoderma Japonicum, Flower Pollen, Panax Ginseng, Glycyrrhiza and Cervus Nippon Temminck in weight ratio ranges with Lycoris Radiata of 1:0.5-2, 1:0.5-2, 1:0.5-2, 1:0.5-2, 1:0,5-2. 1:0.5-2 and 1:0,01-0.2, respectively.

3. A dried ethanol extraction eluate of a residue obtained by boiling water extraction of cut, dried Cheng-min chou.

4. A dried ethanol extraction eluate of a residue obtained by boiling water extraction of cut, dried Mou-hui Tou.

5. A food additive composition comprising a dietary supplementing amount of the composition of claim 1 in an ingestible form.

6. The food additive composition of claim 5 wherein the ingestible form is selected from a powder, capsule or tablet.

7. A food additive composition comprising a dietary supplementing amount of the composition of claim 2 in an ingestible form.

8. An appetite stimulant composition comprising an appetite stimulating amount of the composition of claim 1 in an ingestible form.

9. The appetite stimulant composition of claim 8 wherein the ingestible form is selected from a powder, capsule or tablet.

10. An appetite stimulant composition comprising an appetite stimulating amount of the composition of claim 2 in an ingestible form.

11. A method of stimulating the appetite of an individual in need thereof which comprises administering an appetite stimulating amount of the composition of claim 8.

12. A pharmaceutical composition comprising the composition of claim 2 in an analgesically effective amount in a pharmaceutically acceptable carrier.

13. A pharmaceutical composition comprising the composition of claim 1 in a mood elevant amount in a pharmaceutically acceptable carrier.

14. A pharmaceutical composition comprising the composition of claim 2 in a mood elevant amount in a pharmaceutically acceptable carrier.

15. A method of treating pain in an individual thereof which comprises administering an analgesically effective amount of the composition of claim 12.

16. A method of elevating the mood of an individual in need thereof which comprises administering to said individual a mood elevating amount of the composition of claim 13.

17. A method of supplementing the diet of an individual in need thereof which comprises administering a dietary supplementing amount of the composition of claim 5.

* * * * *